(12) United States Patent
Kantor et al.

(10) Patent No.: US 6,375,983 B1
(45) Date of Patent: Apr. 23, 2002

(54) MICROENCAPSULATED FRAGRANCES AND METHOD FOR PREPARATION

(75) Inventors: Martin L. Kantor, Mamaroneck; Evgueni Barantsevitch, Scarsdale; Sam J. Milstein, Larchmont, all of NY (US)

(73) Assignee: Emisphere Technologies, Inc., Tarrytown, NY (US)

( * ) Notice: Subject to any disclaimer, the term of this patent is extended or adjusted under 35 U.S.C. 154(b) by 0 days.

(21) Appl. No.: 08/873,780

(22) Filed: Jun. 12, 1997

Related U.S. Application Data

(60) Provisional application No. 60/019,913, filed on Jun. 19, 1996.

(51) Int. Cl.$^7$ .............................. A61K 9/14; A61L 9/00; B32B 27/04
(52) U.S. Cl. ..................... 424/489; 424/76.1; 424/76.4; 424/486; 512/3; 442/96
(58) Field of Search ................................ 424/486, 489, 424/464, 496, 59, 184, 76.1, 70.9, 76.2, 76.4; 512/4

(56) References Cited

U.S. PATENT DOCUMENTS

| | | | |
|---|---|---|---|
| 2,671,451 A | 3/1954 | Bolger | 128/260 |
| 2,862,918 A | 12/1958 | Meyer et al. | 260/123.5 |
| 2,868,740 A | 1/1959 | Luce | 260/8 |
| RE24,899 E | 11/1960 | Green | |
| 2,971,916 A | 2/1961 | Schleicher et al. | 252/62.5 |
| 3,016,308 A | 1/1962 | Macaulay | 177/37 |
| 3,052,655 A | 9/1962 | Fox et al. | 260/78 |
| 3,057,344 A | 10/1962 | Abella et al. | 128/2 |
| 3,076,790 A | 2/1963 | Fox et al. | 260/78 |
| 3,170,802 A | 2/1965 | Fukushima | 99/145 |
| 3,190,837 A | 6/1965 | Brynko et al. | 252/316 |
| 3,474,777 A | 10/1969 | Figge et al. | 128/2 |
| 3,491,093 A | 1/1970 | Pachter et al. | 260/247.5 |
| 3,565,559 A | 2/1971 | Sato | 424/37 |
| 3,567,650 A | 3/1971 | Bakan | 252/316 |
| 3,574,832 A | 4/1971 | Engel et al. | 424/183 |
| 3,576,758 A | 4/1971 | Emrick | 252/316 |
| 3,687,926 A | 8/1972 | Arima et al. | 260/112.5 |
| 3,725,113 A | 4/1973 | Chang | 117/82 |
| 3,748,277 A | 7/1973 | Wagner et al. | 252/316 |
| 3,794,561 A | 2/1974 | Matsukawa et al. | 195/29 R |
| 3,795,739 A | 3/1974 | Birkmayer et al. | 424/274 |
| 3,816,404 A | 6/1974 | Kablaoui et al. | 260/239.3 |
| 3,822,348 A | 7/1974 | Higashi et al. | 424/95 |
| 3,849,550 A | 11/1974 | Teitelbaum | 424/78 |
| 3,933,873 A | 1/1976 | Love et al. | 260/239.3 |
| 3,937,668 A | 2/1976 | Zolle | 252/316 |
| 3,939,253 A | 2/1976 | Bodor et al. | 424/309 |
| 3,956,172 A | 5/1976 | Saeki et al. | 252/316 |
| 3,962,416 A | 6/1976 | Katzen | 424/19 |
| 3,976,773 A | 8/1976 | Curran | 424/250 |
| 4,035,507 A | 7/1977 | Bodor et al. | 424/311 |

(List continued on next page.)

FOREIGN PATENT DOCUMENTS

| | | | |
|---|---|---|---|
| CA | 1077842 | 8/1976 | ............ A61K/9/50 |
| DE | 2 424 169 | 12/1974 | ............ A61K/9/00 |
| DE | 2 343 037 | 3/1975 | |
| DE | 3 202 255 | 10/1982 | ............ C08L/89/00 |
| DE | 3 612 102.9 | 10/1986 | ............ C07K/15/00 |
| EP | 0 000 667 A1 | 2/1979 | ............ A61K/9/50 |
| EP | 0 036 145 A1 | 9/1981 | ............ A61K/31/62 |
| EP | 0 067 533 | 12/1982 | ............ B01J/13/02 |
| EP | 0 068 314 | 1/1983 | ............ A61K/31/16 |
| EP | 0 105 804 | 4/1984 | ............ C12N/15/00 |
| EP | 0 130 162 A2 | 1/1985 | ............ B01J/13/02 |
| EP | 0 170 540 A1 | 2/1986 | ............ A61K/9/52 |
| EP | 0 342 054 A2 | 11/1989 | ............ A61K/7/06 |
| EP | 0 342 056 A2 | 11/1989 | ............ A61K/7/06 |
| EP | 0 365 183 | 4/1990 | ......... C07C/311/21 |
| EP | 0 366 277 | 5/1990 | ......... A61K/9/107 |
| EP | 0 418 642 | 3/1991 | .......... A61K/37/30 |
| EP | 0 448 057 | 9/1991 | ............ C12P/21/08 |
| EP | 0 452 161 | 10/1991 | ............ A61K/7/48 |
| EP | 0 459 795 | 12/1991 | .......... A61K/37/02 |
| EP | 0 467 389 | 1/1992 | ............ A61K/9/52 |
| EP | 0 490 549 A1 | 6/1992 | ............ A61K/47/12 |
| EP | 0 517 211 A1 | 9/1992 | ............ A61K/47/12 |
| EP | 0 616 799 A1 | 9/1994 | ............ A61K/7/00 |
| FR | 1 351 358 | 3/1964 | |
| FR | 1 468 601 | 2/1967 | |
| FR | 2 133 926 | 12/1972 | .......... A61K/27/00 |
| FR | 2 326 934 | 5/1977 | .......... A61K/47/00 |
| FR | 2 565 102 | 12/1985 | ............ A61K/9/52 |
| GB | 929401 | 6/1963 | |
| GB | 1 075 952 | 8/1967 | |
| GB | 1 236 885 | 6/1971 | |
| GB | 1 567 763 | 5/1980 | ............ A61K/9/22 |
| GB | 2 095 994 | 10/1982 | ............ A61K/9/00 |
| IL | 71258/2 | 12/1987 | |
| JP | 48-24246 | 3/1973 | |
| JP | 56-68612 | 6/1981 | .......... A61K/31/19 |
| JP | 58-35111 | 3/1983 | ............ A61K/9/66 |
| JP | 06-107682 | 4/1994 | |

(List continued on next page.)

OTHER PUBLICATIONS

Fox, S.W. et al., *Molecular Evolution and the Origin of Life*, Maxel Decker, New York (1977).

Fox, S.W. et al. (1968) *Biochim. Biophys. Acta*, vol. 160, pp. 246–249.

Fox, S.W. (1976) *Origins of Life*, vol. 7, pp. 49–68.

Fox, S.W. (1980) *Naturwissenschaften*, vol. 67, pp. 378–383.

(List continued on next page.)

*Primary Examiner*—Thurman K. Page
*Assistant Examiner*—Blessing Fubara
(74) *Attorney, Agent, or Firm*—Darby & Darby

(57) ABSTRACT

This invention provides an encapsulated fragrance in which the fragrance is controlled can be released by exposing the encapsulated fragrance to a solution of a predetermined pH. The invention also contemplates a process for preparing encapsulated fragrances.

17 Claims, No Drawings

U.S. PATENT DOCUMENTS

| | | | |
|---|---|---|---|
| 4,048,268 A | 9/1977 | Ludwig .................... 264/15 |
| 4,061,466 A | 12/1977 | Sjoholm et al. .......... 23/230 B |
| 4,117,801 A | 10/1978 | Dannelly et al. ............. 118/20 |
| 4,136,250 A * | 1/1979 | Mueller et al. ............... 528/29 |
| 4,147,767 A | 4/1979 | Yapel .......................... 424/22 |
| 4,181,708 A | 1/1980 | Dannelly ..................... 424/19 |
| 4,181,710 A | 1/1980 | Dannelly et al. ............. 424/33 |
| 4,183,849 A | 1/1980 | Hansen .................... 260/112.7 |
| 4,196,187 A | 4/1980 | Dannelly et al. ............. 424/21 |
| 4,199,561 A | 4/1980 | Roth et al. .................... 424/32 |
| 4,217,370 A | 8/1980 | Rawlings et al. ............. 426/98 |
| 4,238,506 A | 12/1980 | Stach et al. ................. 424/319 |
| 4,239,635 A | 12/1980 | Rieder ......................... 252/34 |
| 4,239,754 A | 12/1980 | Sache et al. ................ 424/183 |
| 4,272,506 A | 6/1981 | Schwarzberg .................. 424/8 |
| 4,289,759 A | 9/1981 | Heavner et al. ............ 424/177 |
| 4,345,588 A | 8/1982 | Widder et al. ............... 128/1.3 |
| 4,348,384 A | 9/1982 | Horikoshi et al. .......... 424/101 |
| 4,351,337 A | 9/1982 | Sidman ...................... 128/260 |
| 4,352,883 A | 10/1982 | Lim ........................... 435/178 |
| 4,357,259 A | 11/1982 | Senyei et al. ............... 252/316 |
| 4,388,304 A | 6/1983 | Nyeki et al. ................ 424/177 |
| 4,393,192 A | 7/1983 | Curatolo et al. ............ 528/292 |
| 4,402,856 A | 9/1983 | Schnoring et al. ..... 428/402.22 |
| 4,402,968 A | 9/1983 | Martin ........................ 424/273 |
| 4,405,598 A | 9/1983 | Brown ......................... 424/45 |
| 4,442,090 A | 4/1984 | Kakeya et al. .............. 424/178 |
| 4,446,138 A | 5/1984 | Pack ...................... 424/248.57 |
| 4,450,150 A | 5/1984 | Sidman ........................ 424/1.1 |
| 4,457,907 A | 7/1984 | Porter ......................... 424/7.1 |
| 4,460,563 A | 7/1984 | Calanchi ...................... 424/35 |
| 4,462,839 A | 7/1984 | McGinley et al. .......... 106/198 |
| 4,462,991 A | 7/1984 | Higuchi et al. ............. 424/177 |
| 4,464,271 A | 8/1984 | Munteanu et al. ........... 252/8.6 |
| 4,473,620 A | 9/1984 | Wu et al. ............... 428/402.24 |
| 4,483,807 A | 11/1984 | Asano ......................... 264/22 |
| 4,492,684 A | 1/1985 | Goosen et al. ................ 424/19 |
| 4,518,433 A | 5/1985 | McGinley et al. .......... 106/180 |
| 4,590,265 A | 5/1986 | Bogan et al. ................. 536/63 |
| 4,608,278 A | 8/1986 | Frank .................... 427/213.35 |
| 4,613,500 A | 9/1986 | Suzuki et al. ................. 429/85 |
| 4,647,455 A | 3/1987 | De Bold ...................... 424/95 |
| 4,666,641 A | 5/1987 | Fickat et al. ................. 264/4.3 |
| 4,671,954 A | 6/1987 | Goldberg .................... 424/450 |
| 4,673,566 A | 6/1987 | Gossen et al. ................ 424/19 |
| 4,683,092 A | 7/1987 | Tsang ......................... 264/4.3 |
| 4,690,786 A | 9/1987 | Ninomiya et al. ........... 264/4.6 |
| 4,692,284 A | 9/1987 | Braden ........................ 264/4.3 |
| 4,692,433 A | 9/1987 | Hostetler et al. ............ 514/190 |
| 4,703,042 A | 10/1987 | Bodor ......................... 514/56 |
| 4,708,952 A | 11/1987 | Salatinjants ................. 514/158 |
| 4,745,161 A | 5/1988 | Saudek et al. .............. 525/420 |
| 4,753,804 A | 6/1988 | Iaccheri et al. ............. 424/491 |
| 4,757,007 A | 7/1988 | Satoh .......................... 435/69 |
| 4,757,024 A | 7/1988 | Roper ........................ 436/507 |
| 4,757,066 A | 7/1988 | Shiokari et al. ............. 514/210 |
| 4,766,012 A | 8/1988 | Valenti .................. 427/213.36 |
| 4,774,320 A | 9/1988 | Tagliabue et al. ........... 530/328 |
| 4,780,315 A | 10/1988 | Wu et al. .................... 424/438 |
| 4,789,734 A | 12/1988 | Pierschbacher ............. 530/395 |
| 4,835,312 A | 5/1989 | Itoh et al. .................... 564/205 |
| 4,837,381 A | 6/1989 | Steber et al. ................ 424/502 |
| 4,842,761 A | 6/1989 | Rutherford ................... 252/90 |
| 4,844,904 A | 7/1989 | Hamaguchi et al. ........ 424/450 |
| 4,873,087 A | 10/1989 | Morishita et al. ........... 424/433 |
| 4,878,942 A | 11/1989 | Motegi et al. |
| 4,886,663 A | 12/1989 | Houghten .................... 424/88 |
| 4,895,725 A | 1/1990 | Kantor et al. ............... 424/455 |
| 4,897,444 A | 1/1990 | Brynes et al. ............. 525/54.1 |
| 4,900,730 A | 2/1990 | Miyauchi ..................... 514/12 |
| 4,908,233 A | 3/1990 | Takizawa et al. ....... 427/213.35 |
| 4,919,939 A | 4/1990 | Baker ......................... 424/493 |
| 4,925,673 A | 5/1990 | Steiner ....................... 424/455 |
| 4,927,928 A | 5/1990 | Shroot et al. |
| 4,963,364 A | 10/1990 | Fox et al. ................... 424/455 |
| 4,976,968 A | 12/1990 | Steiner ....................... 424/491 |
| 4,983,402 A | 1/1991 | Steiner ....................... 424/491 |
| 4,996,292 A | 2/1991 | Fox et al. ................... 528/328 |
| 5,019,400 A | 5/1991 | Gombotz et al. ........... 424/497 |
| 5,023,374 A | 6/1991 | Simon ........................ 564/152 |
| 5,039,481 A | 8/1991 | Pacifici et al. ................. 422/4 |
| 5,041,291 A | 8/1991 | Bader et al. ................ 424/426 |
| 5,055,300 A | 10/1991 | Gupta ......................... 424/409 |
| 5,066,487 A | 11/1991 | Morelle et al. ............... 424/68 |
| 5,067,961 A | 11/1991 | Kelman et al. ................ 623/5 |
| 5,069,936 A | 12/1991 | Yen ....................... 427/213.33 |
| 5,077,278 A | 12/1991 | Hafner et al. ................ 514/30 |
| 5,100,669 A | 3/1992 | Hyon et al. ................. 424/426 |
| 5,100,918 A | 3/1992 | Sunshine et al. ........... 514/557 |
| 5,122,367 A | 6/1992 | Ron et al. ..................... 424/80 |
| 5,126,147 A | 6/1992 | Silvestri et al. ............. 424/497 |
| 5,137,892 A | 8/1992 | Chu et al. ................... 514/278 |
| 5,186,947 A | 2/1993 | Goettsche et al. .......... 424/638 |
| 5,204,099 A | 4/1993 | Barbier et al. .............. 424/401 |
| 5,206,384 A | 4/1993 | Shibahara et al. .......... 548/537 |
| 5,216,124 A | 6/1993 | Hansen, Jr. et al. ........ 530/317 |
| 5,244,653 A | 9/1993 | Berke et al. .................. 424/70 |
| 5,246,603 A | 9/1993 | Tsaur et al. ................... 252/86 |
| 5,250,236 A | 10/1993 | Gasco ......................... 264/4.4 |
| 5,271,934 A | 12/1993 | Goldberg et al. ........... 424/401 |
| 5,271,961 A | 12/1993 | Mathiowitz et al. ... 427/213.31 |
| 5,278,148 A | 1/1994 | Branca et al. ................ 514/19 |
| 5,281,357 A | 1/1994 | Morgan et al. .............. 252/174 |
| 5,310,535 A | 5/1994 | Kruper, Jr. et al. ........ 424/1.53 |
| 5,328,992 A | 7/1994 | Peter et al. .................. 534/116 |
| 5,352,461 A | 10/1994 | Feldstein et al. ........... 424/493 |
| 5,384,133 A | 1/1995 | Boyes et al. ................ 424/501 |
| 5,385,959 A | 1/1995 | Tsaur et al. ................. 523/201 |
| 5,389,377 A | 2/1995 | Chagnon et al. ............ 424/450 |
| 5,389,379 A | 2/1995 | Dirix et al. .................. 424/451 |
| 5,401,516 A | 3/1995 | Milstein et al. ............. 424/491 |
| 5,418,010 A | 5/1995 | Janda et al. ............ 427/213.31 |
| 5,439,686 A | 8/1995 | Desai et al. ................. 424/451 |
| 5,443,841 A | 8/1995 | Milstein et al. ............. 424/451 |
| 5,447,728 A | 9/1995 | Milstein et al. ............. 424/490 |
| 5,451,410 A | 9/1995 | Milstein et al. ............. 424/490 |
| 5,474,997 A | 12/1995 | Gray et al. .................. 514/252 |
| 5,492,646 A | 2/1996 | Langley et al. ............. 252/174 |
| 5,508,024 A * | 4/1996 | Tranner ....................... 424/59 |
| 5,536,813 A | 7/1996 | Charpenel et al. .......... 530/324 |
| 5,540,939 A | 7/1996 | Milstein et al. ............. 424/491 |
| 5,541,155 A | 7/1996 | Leone-Bay .................... 514/2 |
| 5,576,286 A | 11/1996 | Karp et al. .................... 512/2 |
| 5,578,323 A | 11/1996 | Milstein et al. ............. 424/499 |
| 5,601,846 A | 2/1997 | Milstein et al. ............. 424/499 |
| 5,629,020 A | 5/1997 | Leone-Bay et al. ......... 424/489 |
| 5,643,957 A | 7/1997 | Leone-Bay et al. ......... 514/563 |
| 5,650,386 A | 7/1997 | Leone-Bay et al. ............ 514/2 |
| 5,665,700 A | 9/1997 | Cho et al. ...................... 514/2 |
| 5,667,806 A | 9/1997 | Kantor ........................ 424/484 |
| 5,693,338 A | 12/1997 | Milstein |
| 5,705,529 A | 1/1998 | Matyus et al. |
| 5,709,861 A | 1/1998 | Santiago et al. |
| 5,714,167 A | 2/1998 | Milstein et al. |
| 5,750,147 A | 5/1998 | Kantor |
| 6,024,943 A | 2/2000 | Ness et al. ..................... 424/59 |

FOREIGN PATENT DOCUMENTS

| | | | | |
|---|---|---|---|---|
| NL | 280825 | 12/1964 | | |
| NL | 280826 | 12/1964 | | |
| NO | B-146698 | 11/1982 | .......... A61K/37/26 |

| | | | |
|---|---|---|---|
| WO | WO 85/00105 | 1/1985 | ............ A61K/9/52 |
| WO | WO 85/00110 | 1/1985 | .......... A61K/47/00 |
| WO | WO 85/00809 | 2/1985 | ........ C07D/233/64 |
| WO | WO 87/04076 | 7/1987 | .......... A61K/45/02 |
| WO | WO 88/1213 | 2/1988 | ............ B23B/5/16 |
| WO | WO 92/19263 | 12/1992 | .......... A61K/39/00 |
| WO | WO 93/18754 | 9/1993 | ............ A61K/9/16 |
| WO | WO 93/25583 | 12/1993 | ........... C07K/15/00 |
| WO | WO 94/11015 | 5/1994 | .......... A61K/37/00 |
| WO | WO 94/14420 | 7/1994 | ............ A61K/9/16 |
| WO | WO 94/18950 | 9/1994 | .......... A61K/9/127 |
| WO | WO 94/18997 | 9/1994 | .......... A61K/37/00 |
| WO | WO 94/21234 | 9/1994 | ............ A61K/7/00 |
| WO | WO 94/23702 | 10/1994 | ............ A61K/9/16 |
| WO | WO 94/23767 | 10/1994 | ............ A61L/9/16 |
| WO | WO 94/24291 | 10/1994 | ........ A61K/39/015 |
| WO | WO 94/28878 | 12/1994 | ............ A61K/9/14 |
| WO | WO 95/11690 | 5/1995 | .......... A61K/37/00 |
| WO | WO 85/02772 | 7/1995 | .......... A61K/49/00 |
| WO | WO 95/28838 | 11/1995 | .......... A01N/37/46 |
| WO | WO 95/28920 | 11/1995 | .......... A61K/31/19 |
| WO | WO 96/12473 | 5/1996 | ............ A61K/9/16 |
| WO | WO 96/12474 | 5/1996 | ............ A61K/9/16 |
| WO | WO 96/12475 | 5/1996 | ............ A61K/9/16 |
| WO | WO 96/21464 | 7/1996 | .......... A61K/39/00 |
| WO | WO 96/30036 | 10/1996 | .......... A61K/38/00 |
| WO | WO 96/33699 | 10/1996 | ............ A61K/9/16 |
| WO | WO 96/39835 | 12/1996 | .......... A01N/43/50 |
| WO | WO 96/40070 | 12/1996 | ............ A61K/9/14 |
| WO | WO 96/40076 | 12/1996 | ............ A61K/9/16 |
| WO | WO 97/10197 | 3/1997 | .......... C07C/51/10 |
| WO | WO 97/31938 | 9/1997 | ............ C07K/5/00 |
| WO | WO 97/36480 | 10/1997 | .......... A01N/37/12 |
| WO | WO 97/47270 | 12/1997 | |
| WO | WO 97/47288 | 12/1997 | |

OTHER PUBLICATIONS

Fox, S.W. et al. (1960) *Archives of Biochemistry and Biophysics*, vol. 86, pp. 281–285.
Fox, S.W. et al. (1974) *Origins of Life*, vol. 5, pp. 227–237.
Fox, S.W. (1984) *Origins of Life*, vol. 14, pp. 485–488.
Gol'dovskii, A.M. (1978) *Zhurnal Evolyutsionnoi Biokhimii i Fiziologii*, vol. 14(6), pp. 437–439.
Gurrieri, S. et al. (1973) *Thermochimica Acta*, vol. 7, pp. 231–239.
Harada, K. et al. (1979) *BioSystems*, vol. 11, pp. 47–53.
Harada et al., (1960) *Archives of Biochemistry and Biophysics*, vol. 86, pp. 274–280.
Hare (1970) *Etude Cenetique De La Polycondensation Thermique D'$_X$–Amino Acides*, vol. 45, pp. 330–339.
Heinrich, M.R. et al. (1969) *Archives of Biochemistry and Biophysics*, vol. 130, pp. 441–448.
Heinz, B. et al. (1981) *BioSystems*, vol. 14, pp. 33–40.
Hennon, G. et al. (1975) *Biochimie*, vol. 57, pp. 1395–1396.
Hsu, L.L. et al. (1976) *BioSystems*, vol. 8, pp. 89–101.
Hsu, L.L. et al. (1971) *Currents in Modern Biology*, vol. 4, pp. 12–25.
Ishima, Y. et al. (1981), *BioSystems*, vol. 14, pp. 243–251.
Jackson et al. (1991) "Pharmacological . . .", *J. Pharm. & Exp. Thera.*, vol. 261, No. 1, pp. 546–552.
Jungck, J.R. et al. (1973) *Naturwissenschaften*, vol. 60, pp. 425–427.
Kokufuta, E. et al. (1984) *BioSystems*, vol. 16, pp. 175–181.
Krampitz, G. et al. (1967) *Naturwissenschaften*, pp. 516–517.
Krampitz, G. et al. (1968) *Naturwissenschaften*, pp. 345 and 346.

Krampitz, G. et al. (1966) *Naturwissenschaften*, pp. 7 and 8.
Lacey, Jr., J.C. et al. (1979) *BioSystems*, vol. 11, pp. 9–17.
Lacey, Jr., J.C. et al. (1979) *BioSystems*, vol. 11, pp. 1–7.
Martinez Luque–Romero, M. et al. (1986) *BioSystems*, vol. 19, pp. 267–272.
Masinovsky, Z. et al. (1989) *BioSystems*, vol. 22, pp. 305–310.
Matsuno, K. (1982) *BioSystems*, vol. 15, pp. 1–11.
Matsuno, K. (1984) *BioSystems*, vol. 17, pp. 11–14.
Matsuno, K. (1981) *BioSystems*, vol. 14, pp. 163–170.
McAlhaney, W.W. et al. (1976) *BioSystems*, vol. 8, pp. 45–50.
Melius, P. et al. (1987) *BioSystems*, vol. 20, pp. 213–217.
Melius, P. et al. (1975) *Bioorganic Chemistry*, vol. 4, pp. 385–391.
Melius, P. (1979) *BioSystems*, vol. 11, pp. 125–132.
Miquel, J. et al. (1971) *Currents in Modern Biology*, vol. 3, pp. 299–306.
Nakashima, T. et al. (1980) *J. Mol. Evol.*, vol. 15, pp. 161–168.
Nakashima, T. et al. (1981) *BioSystems*, vol. 14, pp. 151–161.
Novak, V.J.A. (1984) *Origins of Life*, vol. 14, pp. 513–522.
Olafsson, P.G. et al. (1971) *Polymer Letters*, vol. 9, pp. 521–528.
Phillips, R.D. et al. (1974) *Int. J. Peptide Protein Res.*, vol. 6, pp. 309–319.
Przybylski, A.T. et al. (1982) *Die Naturwissenschaften*, vol. 69, pp. 561–563.
Przybylski, A.T. et al. (1984) *Applied Biochemistry and Biotechnology*, vol. 10, pp. 301–307.
Przybylski, A.T. (1985) *BioSystems*, vol. 17, pp. 281–288.
Rohlfing, D.L. (1975) *Origins of Life*, vol. 6, pp. 203–209.
Rohlfing, D.L. (1970) *Science*, vol. 169, pp. 998–1000.
Rohlfing, D.L. (1967) *Archives of Biochemistry and Biophysics*, vol. 118, pp. 468–474.
Rohlfing, D.L. et al. *Catalytic Activities of Thermal Polyanhydro–α–Amino Acids*, pp. 373–418, 1969.
Rohlfing, D.L. et al. (1976) *BioSystems*, vol. 8, pp. 139–145.
Ryan, J.W. et al. (1973) *BioSystems*, vol. 5, pp. 115–118.
Saunders, M.A. et al. (1974) *BioSystems*, vol. 6, pp. 81–92.
Snyder, W.D. et al. (1975) *BioSystems*, vol. 7, pp. 222–229.
Sokol, P.E. (1974) *Journal of the American Oil Chemists'Society*, vol. 52, pp. 101–102.
Tschager et al. (1988) *Milchwirtschaftliche Berichte*, vol. 95, pp. 79–83.
Vaughan, G. et al. (1987) *BioSystems*, vol. 20, pp. 219–223.
Vol'kenshtein, M.V. (1989) *Molekulyarnaya Biologiya*, vol. 23(1), pp. 23–37.
Waehneldt, T.V. et al. (1968) *Biochim. Biophys. Acta*, vol. 160, pp. 239–245.
Williams et al. (1991) *J. Biol. Chem.*, vol. 266, No. 8, pp. 5182–5190.
Yuki, A. et al. (1969) *Biochemical and Biophysical Research Communications*, vol. 36(4), pp. 657–663.
Zulaski et al. (1983) "New Carboxyalkyl Inhibitors of Brain Enkenphalinase", *J. Med. Chem.*, 26, pp. 60–65.
(1985) *Chemical Abstracts*, vol. No. 105(1), Abstract No. 12027p.
(1985) *Chemical Abstracts*, vol. No. 102(6), Abstract No. 50870d.
*Chemical Abstract*, vol. 80(9) Abst. No. 52392a.

Bergeron, Raymond J., et al. (1994) "Macromolecular Self-Assembly of Diketopiperazine Tetrapeptides", *Journal of the American Chemical Society*, vol. 116, pp. 8479–8484.

Bergeron, Raymond J., et al. (1993) "A Comparative Study of the Iron–Clearing Properties of Desferrithiocin Analogues With Desferrioxamine B in a Cebus Monkey Model", *Blood*, vol. 81, No. 8, pp. 2166–2173.

Bergeron, Raymond J., et al. (1992) "A Comparison of the Iron–Clearing Properties of 1,2–Dimethyl–3–Hydroxypyrid–4–One, 1,2–Diethyl–3–Hydroxypyrid–4–One, and Deferoxamine", *Blood*, vol. 79, No. 7, pp. 1882–1890.

Bergeron, Raymond J., et al. (1991) "Evaluation of Desferrithiocin and Its Synthetic Analogs as Orally Effective Iron Chelators", *Journal of Medicinal Chemistry*, vol. 34, No. 7, pp. 2072–2078.

Bergeron, Raymond et al., "A Comparative Evaluation of Iron Clearance Models", *Annals New York Academy of Sciences*, pp. 278–393, Mar. 13–15, 1990.

Andriuoli, G., et al. (1990), *Haemostasis* 20 (suppl. 1):154–158.

Caramazza, I., et al. (1991), *Thrombosis Research* 62:785–789.

Guarini, S., et al. (1983), *Experimentia* 41:350–352.

Guarini, S., et al. (1985), *Pharmacological Research Communications* 17(8):685–697.

Dal Pozzo, A., et al. (1989), *Thrombosis Research* 56:119–124.

Gelb, R., et al (1983), *Lite Sciences* 33(1):83–85.

Watterberg et al. (1988), *Pediatric Research*, vol. 23, No. 4, part 2, p. 570A, column 1, abstract No. 2209.

Bernstein (1985), *Chest* 87(1):68S–73S.

Damge et al. (1988), *Diabetes* 37:246–251.

*Chemical Abstracts*:83 184360k, (1975).

Amino, Y., et al., *Chem. Pharm. Bull.* 36(11):4426–4434 (1988).

Baughman, R.A. et al., *Proc. of the 6th Inter'l. Symp. on Recent Advs. in Drug Delivery Systems, Ctr. for Controlled Chem. Delivery*, University of Utah, Feb. 22–25, 1993, Salt Lake City, UT, pp. 179–180 "Method for Assessing The Stability of Proteinoid Microspheres".

Haas, S. et al., "Assessment Of Stability Of Proteinoid Microspheres", *Proceed. Intern. Symp. Control. Rel. Bioact. Mater.*, 20 (1993), Controlled Release Society, Inc.,.

X. Ma, et al., *Proceed. Intern. Symp. Control. Rel. Bioact. Mater.*, 20 (1993), Controlled Release Society, Inc. "In Vitro Mechanistic Investigation of the Proteinoid Microsphere Oral Delivery System".

Yen, H.–R H., et al., "Adsorption of Sulforhodamine 101 on Proteinoid Microspheres" *Proceed. Intern. Symp. Control. Rel. Bioact. Mater.*, 20 (1993), Controlled Release Society, Inc.

Presented at "*IBC Rational Drug Design Conference*", San Diego, Calif.—Dec. 1994.

Leone–Bay et al., Presented at "*Winter Conference on Medicinal and Bioorganic Chemistry*" Steamboat Springs, Colorado—Feb. 1995 "Microsphere Formation and Drug Delivery in a Series of Derivatized Amino Acids".

Santiago et al., *Pharm. Res.* 11: 1994, p. S–298 "Oral Delivery of Heparin Microspheres made with Modified Amino Acids".

Leone–Bay et al., *Pharm. Res.* 11: 1994, p. S–121 "Oral Delivery of Heparin using Acylated Amino Acids".

Sarubbi et al., *Pharm. Res.* 11: 1994, p. S–299 "Oral Calcitonin Delivery using the PODDS Technology".

Leipold et al., *Pharm. Res.* 11: 1994, p. S–298 "Oral Delivery of Interferon in Rats and Primates".

Santiago et al., *Pharm. Res.* 11: 1994, p. S–298 "Evaluation in Rats of Vehicles for the Oral Delivery of Low Molecular Weight Heparin".

X. Ma et al., PDD 7303 *Pharmaceutical Research* 9(10):S–244, 1992 (Oct. Supplement).

Milstein et al., *Symposia Abstracts*. AAPS Annual Meeting, San Antonia, TX, Nov. 15–19, 1993.

Santiago et al. "Initial Studies In The Assessment of Proteinoid Microsphere Activity" *Proceed. Intern. Symp. Control. Rel. Bioact. Mater.*, 20 (1993), Controlled Release Society, Inc.

Santiago et al. "Oral Immunization of Rats with Influenza Virus M Protein (M1) Microspheres" *Proceed. Intern. Symp. Control. Rel. Bioact. Mater.*, 19 (1992), Controlled Release Society, Inc., p. 116–117.

Santiago et al. "Proteinoid Microspheres For The Oral Delivery of Heparin" *Proceed. Intern. Symp. Control. Rel. Bioact. Mater.*, 19 (1992), Controlled Release Society, Inc. p. 514–515.

Santiago et al. *American Society for Microbiology* 92nd General Meeting, Abstract of the General Meeting, p. 159, May 26–30, 1992.

Milstein et al. "Preparation And In Vitro Characterization Of Proteinoid Microspheres" *Proceed Intern. Symp. Control. Rel. Bioact. Mater.*, 19 (1992), Controlled Release Society, Inc. p. 516–517.

Doris K. Chiappetta, *Eastern Analytical Symposium*, Nov. 17, 1992 "Solutions for Problems in Bioanalysis".

Elizabeth A. Harris. M.S., *Eastern Analytical Symposium*, Nov. 17, 1992 "Solutions for Problems in Bioanalysis".

*AAPS 6TH Ann. Meeting and Expo.*, "Proteinoids—A Novel Drug Delivery System" Nov. 19, 1992, p. 33.

Milstein et al., "Efficient Oral Delivery Of Monoclonal Antibodies By Proteinoid Encapsulation" *The 1993 Miami Bio/Technology Winter Symposium—Advances in Gene Technology: Protein Engineering and Beyond*, Jan. 17–22, 1993.

Xinghang Ma, et al. "Stability Study of Drug–loaded Proteinoid Microsphere Formulations during Freeze–drying" *Journal of Drug Targeting*, 1994, vol. 2, pp 9–21.

Baughman et al., "Screening Candidate Microsphere Formulations By Incubating In Simulated Digestive Fluids" *Proc. of the 6th Intern'l. Sympo. on Recent Advances in Drug Delivery Systems*, Ctr. for Controlled Chem. Delivery, University of Utah, Feb. 22–25, 1993, pp. 181–182.

Robert O. Dillman, M.D., *Annals of Internal Medicine* 1989:111 pp. 592–600, "Monoclonal Antibodies for Treating Cancer".

Brendan D. Curti, *Critical Reviews in Oncology/Hematology*, 1993: 14 pp. 29–39 "Physical barriers to drug delivery in tumors".

V. Hird et al, *Genes and Cancer*, edited by Desmond Carney & Karol Sikora, pp. 183–189, Immunotherapy with Monoclonal Antibodies.

Michael E. Osband et al., *Immunology Today*, vol. 11, No. 6 1990, pp. 193–195, "Problems in the investigational study and clinical use of cancer immunotherapy".

William J. Harris, *Tibtech* Feb. 1993 vol. 11, pp. 42–44 "Therapeutic antibodies—the coming of age".

Thomas A. Waldmann, *Science*, Jun. 21, 1991, 252:1657–1662, "Monoclonal Antibodies in Diagnosis and Therapy".
*Chemical Abstracts*, 76(14):72994u, (1971).
*Chemical Abstracts*, 84(7):44660d, (1975).
*Chemical Abstracts*, 86(16):107529g, (1976).
*Chemical Abstracts*, 112(15):134663h, (1989).
*Chemical Abstracts*, 114(22):214519x, (1990).
J. Györe et al., *Thermal Analysis*, vol. 2—Proceeding Fourth ICTA Budapest 1974, p. 387–394.
*Chemical Abstracts*, 99(19) 158832b, (1982).
*Derwent Abstracts*, JP 67008622, (1967).
*Journal of Medicinal Chemistry*, vol. 38, No. 21, pp. 4257–4262, (1995), "Microsphere Formation in a Series of Derivatized α–Amino Acids: Properties, Molecular Modeling, and Oral Delivery of Salmon Calcitonin".
Andrea Leone–Bay et al., *Journal of Medicinal Chemistry*, vol. 38, No. 21, pp. 4263–4269, (1995), "N–Acylated α–Amino Acids as Novel Oral Delivery Agents for Proteins".
*The Extra Pharmacopoeia*, Thirtieth Edition, pp. 325–326, (1993).
Stephen J. Douglas et al., *Chemistry and Industry*, vol. 22:748–751, 1985.
C.A. Finch, *Chemistry and Industry*, vol. 22:752–756, 1985.
John A. Butera et al., *J. Med. Chem.*, vol. 34:3212–3228, 1990.
Madeline G. Cimini et al., *Ann. Report in Med Chem.*, vol. 27:89–98., 1992.
Bernadette Earley et al., *Brain Research*, vol. 546:282–286, 1991.
John W. Ellingboe et al., *J. Med Chem.*, vol. 35:705–716, 1992.
William C. Lumma et al., *J. Med Chem.*, vol. 30:758–763, 1987.
Joseph J. Lynch et al., *J. of Pharm. and Exp. Therap.*, vol. 269:541–554, 1994.
Kiyoshi Matsuno et al., *Brain Research*, vol. 575:315–319, 1992.
Thomas K. Morgan et al., *J. Med. Chem.*, vol. 33:1091–1097, 1990.
Hitoshi Oinuma et al., *J. Med Chem.*, vol. 33:903–905, 1990.
Tadimeti S. Rao et al., *Molecular Pharmacology*, vol. 37:978–982, 1990.
Asaji Kondo, *Microcapsule Processing and Technology*, pp. 154–165, 1979.
G. Pastores et al., *J. Liquid Chromatography*, 18(15):3049–3059, 1995.
D. Sinha et al., *J. Bio. Chem.*, 260(19):10714–10719. 1985.
E. Franssen et al., *J. Med. Chem.*, 35:1246–1259, 1992.
*Chemical Abstracts*, 99(23):191473h, Dec. 05, 1983.
R. Langer, *Science*, 249:1528, Sep. 28, 1990.
M. Alonso et al., *Vaccine*, 12:299, 1994.
A. Leone–Bay et al., *J. Med. Chem.*, 39:2571–2578, 1996.
R. Thompson, *Biochemistry*, 12:47–51, 1973.
S. Thompson, *J. Med. Chem.*, abstract, 86:174780, 1986.

* cited by examiner

MICROENCAPSULATED FRAGRANCES AND METHOD FOR PREPARATION

This application claims priority pursuant to 35 U. S.C. §119 from U.S. Provisional Application Ser. No 60/019,913 filed Jun. 19, 1996.

This invention relates to an encapsulated fragrance in which the fragrance is controlled can be released by exposing the encapsulated fragrance to a solution of a predetermined pH. The invention also contemplates a process for preparing encapsulated fragrances.

BACKGROUND OF THE INVENTION

There are numerous uses for a system which can release a fragrance in a controlled manner. These include the use of fragrances in substrates such as air fresheners, laundry detergents, fabric softeners, deodorants, lotions, and other household items. However, the design of a system that will release a fragrance over a period of time under repeatable predetermined conditions, has proved difficult. One problem in achieving such a design is that fragrances are generally essential oils that are composed of a plurality of compounds, each present in different quantities. Thus, it is difficult to predict how the quantity of each component of the essential oil will effect the release characteristics of the system.

U.S. Pat. No. 4,587,129 describes a method for preparing gel articles which contain up to 90% by weight of fragrance or perfume oils. The gels are prepared from a polymer having a hydroxy (lower alkoxy) 2-alkeneoate, a hydroxy (lower alkoxy) lower alkyl 2-alkeneoate, or a hydroxy poly (lower alkoxy) lower alkyl 2-alkeneoate and a polyethylenically unsaturated crosslinking agent. These materials are said to have continuous slow release properties, i.e., they release the fragrance component continuously over a long period of time. However, a drawback of the invention is that the release of the fragrance from the gels is continuous and cannot be controlled. Thus, the fragrance can be exhausted while the product in which it is contained is on the shelf, e.g., in storage, prior to use by the consumer.

A composition that functions to hold a fragrance until it is desirable to release the fragrance and then functions to release the fragrance over an extended period of time would be desirable. Thus, an object of this invention is to provide a composition which retains a fragrance until the desired time for release.

SUMMARY OF THE INVENTION

The subject invention provides compositions comprising a polymer and a fragrance, wherein said polymer comprises an acrylic acid copolymer. The acrylic acid copolymer comprises an acrylic acid monomer having the formula:

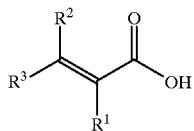

wherein $R^1$, $R^2$, and $R^3$ are independently selected from the group consisting of hydrogen and lower alkyl; and at least one ethylenically unsaturated polymerizable monomer such as acrylates, methacrylates, vinyl pyridines, vinyl ethers, acrylamides, methacrylamides, styrenes, pyrrolidones, and the like.

The fragrances useful in practicing the invention include any material which can impart a desirable odor or enhance an existing smell or odor to a substrate such as, for example air fresheners, laundry detergents, fabric softeners, deodorants, lotions, and other household items. Such fragrances generally contain at least one essential oil.

The compositions of the invention can controllably release a fragrance over an extended time period by contacting the composition with a solution having a pH which dissolves the polymer and releases the fragrance. In another embodiment, the polymer compositions of the invention may be used to form microspheres containing the fragrance.

Also contemplated is a method for preparing these compositions which comprises mixing the monomers and a fragrance and polymerizing the mixture.

DETAILED DESCRIPTION OF THE INVENTION

The present invention provides compositions which are useful for controlled release of fragrances. The compositions of the invention can encapsulate a fragrance and controllably release the fragrance upon exposure to a solution having a predetermined pH. The compositions of the invention comprise a polymer and a fragrance. The polymers useful in practicing the invention can encapsulate the fragrance and release it at the desired time. Any fragrance which can be solubilized in the organic phase of a polymerization emulsion, and which can add a smell or odor to a substrate or is desirable to change, improve or enhance an existing smell or odor of a substrate may be incorporated in the polymers.

The polymers useful in practicing the present invention comprise
 (a) an acrylic acid monomer and
 (b) a second monomer having at least one polymerizable ethylenically unsaturated group, such as, for example, acrylates, methacrylates, vinyl pyridines, vinyl ethers, acrylamides, methacrylamides, pyrrolidones, styrenes, methacrylates, and the like.

The acrylic acid monomer has the formula:

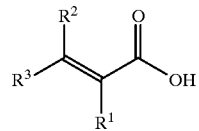

wherein $R^1$, $R^2$, and $R^3$ are independently selected from the group consisting of hydrogen and lower alkyl. These polymers can be used to encapsulate the fragrance until it is desired to release it.

The lower alkyl groups include groups having from 1 to about 6 carbon atoms. Preferred groups are methyl, ethyl, isopropyl and butyl.

Typically, fragrances or perfume agents are compounds or compositions that either increase or enhance an existing smell or odor, or that impart a specific agreeable smell or odor to a substrate. These fragrances may be solids, liquids, vapors, or any combination thereof. Furthermore, they may completely or partially change state before being incorporated into a microsphere, while incorporated in a microsphere, or after being partially or completely released from a microsphere. Non-limiting examples of fragrances include essential oils, such as, for example, d-limonene, eugenol, orange, lemon, eucalyptol (cineol), clove oil and the like. Also useful in practicing the invention are commercially available fragrances which include materials, such as, for example, Autre Melange, or MixTex 1 from Givaudan-Roure, France and the like.

The amount of acrylic acid monomer in the polymer can vary from about 20% to about 80% by weight. The preferred amount of acrylic acid is from about 40% to about 60% by weight.

The release of the fragrance can be controlled by the incorporation of a pH sensitive group in the polymer composition. Examples of pH sensitive groups include carboxyl and amine groups. It is then possible to protonate the amine groups or deprotonate the carboxyl groups to dissolve the polymers and release the fragrance.

The polymers of the invention are prepared by suspension polymerization. The monomers are emulsified with water and the resulting microglobules are polymerized in situ to solid microspheres. If an organic compound, such as most perfumes and fragrances, is added to the unpolymerized mixture, it will partition into the globules. During the polymerization, the fragrance compound becomes incorporated into the polymer or polymer microspheres and protected from volatilization.

These monomers are easy to polymerize and have a strong affinity for the perfume and fragrance materials. The polymerization can be initiated by methods that are well known to those skilled in the art, such as, for example, free-radical initiators, ultraviolet light; heat and the like. Non-limiting examples of free-radical initiators include 2-2', azobisisobutyronitrile (AIBN), benzoyl peroxide, cumene hydroperoxide, and the like. Suspending agents such as polyvinyl alcohol or polyvinylpyrrolidone may also be added to prevent the globules from agglomerating. If a water-soluble monomer is employed, neutral salts such as chlorides and sulfates can be added to cause phase separation.

The suspension polymerization reaction is stirred using standard equipment. The stirring rate is usually from about 200 RPM to about 800 RPM. The preferred rate is from about 250 RPM to about 400 RPM.

Polymerization can be carried out using standard additives known in the art. Examples of additives include stabilizers to reduce agglomeration; salts to reduce phase separation.

Non-limiting examples of stabilizers (suspending agents) include but are not limited to polyvinyl alcohol (PVA), polyvinyl pyrrolidone (PVP), polyacrylic acid (PAA), starch, gelatin, hydroxypropylmethyl cellulose phthalate (HPMCP) and the like. The stabilizing additives can be added in a range of from about 0.1 to about 5 percent and preferably at about 0.3 to about 1.0 percent.

Non-limiting examples of salts which are useful in practicing the invention are chlorides such as sodium chloride, potassium chloride, lithium chloride, calcium chloride, magnesium chloride and the like; or sulfates such as sodium sulfate, potassium can be released when contacted by a solution at the predetermined pH.

Using the conditions described herein, the polymers form hollow or solid matrix type microspheres wherein the cargo/fragrance is distributed in a carrier matrix or capsule type microspheres encapsulating liquid, vapor, or solid cargo. The amount of fragrance which may be incorporated by the microsphere is dependent on a number of factors which include the amount of material mixed with the monomer solution, as well as the affinity of the fragrance agent for the monomers. The polymer microspheres do not alter the properties of the fragrance. Any fragrance can be incorporated within the microspheres. The system is particularly advantageous for controlling the delivery of fragrance to a specific place and/or at a specific time. The targets can vary depending upon the fragrance employed.

The preferred microspheres have diameters between about 1 microns and about 500 microns, preferably between about 100 microns and about 250 microns. The microspheres can be readily blended with other solid or liquid ingredients which require a sustained release of a fragrance or a perfume agent, i.e., detergents, fabric softeners or lotions.

The size of the polymer microspheres formed by the method described herein can be controlled by manipulating a variety of physical or chemical parameters, such as the speed of the mixing during polymerization, monomer composition and the chemical structure of the fragrance.

The monomers, reagents and other additives used in practicing the present invention are commercially available from suppliers such as Aldrich Chemical Co. (Milwaukee, Wis., USA); Sigma Chemical Co. (St. Louis, Mo., USA); and Fluka Chemical Corp. (Ronkonkoma, N.Y., USA).

EXAMPLES

The following examples illustrate the invention without limitations. All monomers are used as received from the supplier, and may contain a small amount of inhibitor. The perfumes used, "MixTex 1" and Autre Melange" are available from Givaudan-Roure and contain several components. Cineole, also called "Eucalyptus Oil", and limonene are aroma materials used for trial encapsulations. The PVA employed in these examples had a M.W. of about 31–50,000 and was 87–89% hydrolyzed.

Example 1

In a flask equipped with a mechanical stirrer, a thermometer, a reflux condenser and inert gas inlet, 0.6 g of polyvinyl alcohol (PVA) was dissolved in 120 ml of distilled water at about 75–80° C. A solution consisting of 14.1 g of butyl methacrylate, 16.1 g of methacrylic acid, 0.9 g of benzoyl peroxide, and 2.3 g of the fragrance Autre Melange was then added to the PVA solution with continuous stirring, at 300 RPM, to produce an emulsion. The formation of solid particles began about 30–40 minutes after the organic monomer solution was added. The reaction temperature was raised from 80° C. to about 90–95° C. at the end of the polymerization process. Polymerization was complete after about 4–5 hours and the suspension was allowed to cool to ambient temperature. The solid product was filtered, washed with water, and dried at ambient temperature. The yield was quantitative.

Under an optical microscope the reaction product was shown to consist of smooth beads having diameters of 100–200$\mu$. The dry beads had no detectable odor. However, they release a strong aroma on being dissolved in water at pH >8.0. The content of methacrylic acid in the co-polymer (based on potentiometric titration data) was 48%.

Example 2

Following the procedure of Example 1, co-polymerization of methacrylic acid and styrene in the presence of the fragrance Autre Melange was effected. A mixture comprising g of methacrylic acid, g of styrene, 3.2 g of benzoyl peroxide, and 11 g of fragrance was emulsified in 480 ml of 0.5% PVA in water, and polymerized at 80–90° C. for 5 hours. Polymer beads having diameters of 70–120$\mu$, 114 g, were obtained. A methacrylic acid content of 46% in the co-polymer was found. The odorless beads release a strong scent of perfume when dissolved in water at a pH >8.0.

Example 3

Following the procedure of Example 1, a mixture of 14.5 g of methacrylic acid, 12.8 g of ethyl methacrylate, 0.7 g of AIBN, and 2.1 g of Autre Melange fragrance was emulsified with 120 ml of 0.5% PVA in water and polymerized at 65–75° C. for 4.5 hours, 29.7 g of the polymer beads having diameters of 40–100μ were obtained. The odorless beads dissolved at pH >8.0 and released a strong scent of perfume.

Example 4

Following the procedure of Example 1, a mixture of 9.2 g of methacrylic acid, 19.8 g of methyl methacrylate, 0.8 g of benzoyl peroxide, and 1.4g of the fragrance Autre Melange was emulsified in 120 ml of 0.5% PVA in water and polymerized at 70–85° C. for 3 hours. 26 g of beads were obtained. The encapsulated fragrance was released more slowly due to the lower solubility in basic water of the co-polymer which contained only 31% of methacrylic acid.

Examples 5–21

Following the procedure of Example 1, polymers with encapsulated Autre Melange fragrance were obtained. The monomers, stabilizer and encapsulation results are tabulated in Table I. These examples produced odorless beads which were soluble at pH >8.0 and released a strong scent of perfume.

Example 22

Following the procedure of Example 1, a mixture of 13.5 g of methacrylic acid, 12.2 g of butyl methacrylate, 0.8 g of benzoyl peroxide, and 3.0 g of cineole was emulsified with 120 ml of 0.5% PVA in water and polymerized at 80–90° C. for 4 hours. Smooth beads, 28.7 g, having diameters of 100–120μ were recovered. The copolymer contained 46% of methacrylic acid and released a strong specific smell of eucalyptus oil when dissolved in basic water at pH >8.0. The copolymer encapsulated 70% of the cineole from the reaction mixture, based on gas chromatography analysis.

Examples 23–26

Following the procedure of Example 22, polymers with encapsulated Limonene or Cineole fragrance were prepared. The monomers, amount of fragrances and encapsulation results are tabulated in Table 2. These examples produced odorless beads which were soluble at pH >8.0 releasing a strong scent of fragrance.

TABLE 1

| Example No. | Monomers[1] | Stabilizer[2] Type/% | Wt. % Fragrance Added/Found[3] | Yield (wt %) | % RCOOH Added/Found[3] | % COOH Found[3] | Particle size [μ]/shape | Shape |
|---|---|---|---|---|---|---|---|---|
| 5 | MAA:MMA | PVA/.5 | 5.0/3.3 | 93 | 52/52 | 27.3 | 100–200 | round |
| 6 | MAA:MMA | PVA/.5 | 7.0/ | 87 | 46.5/43 | 22.4 | 50–120 | smooth round |
| 7 | MAA:Sty | PVA/.5 | 6.5/ | 90.2 | 45.4/43.8 | 22.9 | 100–150 | various |
| 8 | MAA:Sty | PVA/.5 | 6.7/ | 74.5 | 45.2/44.0 | 23.0 | 40–110 | various |
| 9 | MAA:BuMA | PVA/.5 | 6.9/ | 82.7 | 48.2/48.2 | 25.2 | 100–200 | smooth round |
| 10 | MAA:BuMA | PVA/.5 | 7.5/ | 90.1 | 57.7/57.2 | 29.9 | ~100 | various |
| 11[4] | MAA:BuMA | PVA/.5 | 6.9/ | 88.0 | 47.9/41.5 | 21.7 | .3–5 mm | irregular |
| 12 | MAA:BuMA | PVA/.5 | 7.0/ | 93.5 | 48.0/46.9 | 24.5 | 70–120 | smooth |
| 13[7] | MAA:BuMA | PVA/.5 | 7.0/ | 97.3 | 41.8/45.7 | 23.9 | 100–180 | smooth round |
| 14 | MAA:EMA | PVA/.5 | 8.0/ | 94.7 | 47.4/48.6 | 25.4 | 90–120 | round uniform |
| 15 | MAA:EMA | PVA/.5 | — | 99.4 | 51.4/50.9 | 26.6 | 50–100 | round jagged |
| 16[5] | MAA:EMA | PVA/.5 | 7.0/ | 87.8 | 47.4/47.6 | 24.9 | 100–150 | round tendency to aggregate |
| 17[5] | MAA:EMA | PVA/.5 | 7.0/ | 98.9 | 48.2/49.2 | 25.7 | 40–100 | round tendency to aggregate |
| 18[6] | MMA:BuMA | PVA/.5 | 7.0/ | 83 | 48/45.3 | 23.7 | | Aggregates |
| 19 | MAA:BuMA | PVA/.5 | 9.1/ | 98.1 | 47.1/48.1 | 25.14 | 70–120 | round |
| 20 | MAA:BuMA | PVA/.5 | 9.0/ | 99.5 | 47.2/47.6 | 24.91 | 70–120 | round |
| 21 | MAA:Sty | PVA/.5 | 9.0/ | 94.6 | 50.0/46.1 | 24.1 | 70–120 | various |

[1]Monomers - MMA = methyl methacrylate, MAA = methacrylic acid, Sty = styrene, BuMA = butyl methacrylate, EMA = Ethyl Methacrylate
[2]Stabilizers - PVA = polyvinyl alcohol; PAA = polyacrylic acid
[3]Found after analysis of polymer
[4]Water solution contained 7.5% of sodium sulfate
[5]AIBN initiator
[6]Sonicated before polymerization, stirring speed 600 RPM.
[7]Aqueous/organic phase ratio 5:1, 7.5% of salt 340 RPM.

TABLE 2

| Example No. | Monomers[1] | Stabilizer[2] Type/% | Wt. % Fragrance | Fragrance | Yield (wt %) | % COOH Found[3] | Particle size [μ]/shape | Shape |
|---|---|---|---|---|---|---|---|---|
| 23 | MAA:BuMA | PVA/.5 | 10.0 | Limonene | 97.3 | 23.7 | 100–130 | round |
| 24 | MAA:BuMA | PVA/.5 | 10.2 | Cineole | 96.8 | 24.0 | 100–120 | round |
| 25 | MAA:BuMA | PVA/.5 | 24.9 | Cineole | 89.4 | 21.1 | 100–180 | round |
| 26 | MAA:BuMA | PVA/.5 | 34.7 | Cineole | 80.1 | 18.8 | 75–100 | round |

Legend for Table 2
[1]Monomers - MAA = methacrylic acid, BuMA = butyl methacrylate
[2]Stabilizer - PVA = polyvinyl alcohol.
[3]Found after analysis of polymer.

Examples 27–29

Following the procedure of Example 1, polymers containing MixTex 1 fragrance were prepared. The monomers, amounts of fragrance and encapsulation results are tabulated in Table 3. These examples produced odorless beads which were soluble at pH >8.0 releasing a strong scent of fragrance.

TABLE 3

| Example No. | Monomers[1] | Stabilizer[2] Type/% | Wt. % Fragrance | Yield (wt %) | % RCOOH Added/Found[3] | % COOH Found[3] | Particle size [μ]/shape | Shape |
|---|---|---|---|---|---|---|---|---|
| 27[4] | MAA:EMA | PVA/.5 | 7.0 | 90.7 | 48.3/48.2 | 25.2 | 100–200 | round tendency to aggregate |
| 28 | MAA:EMA | PVA/.5 | 7.0 | 66.6 | 47.7/45.1 | 23.6 | 80–130 | round tendency to aggregate |
| 29 | MAA:EMA | PVA/.5 | 7.0 | 75.5 | 47.3/48.4 | 25.3 | 40–70 | round tendency to aggregate |

Legend
[1]Monomers - MAA = methyl acrylic acid, EMA = Ethyl Methacrylate
[2]Stabilizers - PVA = polyvinyl alcohol; PAA = polyacrylic acid
[3]Found after analysis of polymer
[4]Water solution contained 5% of sodium sulfate All patents, applications, publications, and test methods cited herein are hereby incorporated by reference.

What is claimed is:

1. A composition for delivering a desirable fragrance to a substrate, consisting essentially of:

(a) a copolymer consisting of about 20% to about 80% by weight of an acrylic acid monomer and at least one ethylenically unsaturated polymerizable monomer, and (b) at least one fragrance material encapsulated within said copolymer.

2. The composition according to claim 1, wherein said acrylic acid monomer has the formula

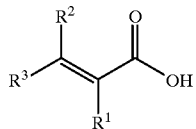

wherein $R^1$, $R^2$ and $R^3$ are independently selected from the group consisting of hydrogen and lower alkyl.

3. The composition according to claim 2, wherein said lower alkyl is a $C_1$–$C_6$ alkyl.

4. The composition according to claim 3, wherein said $C_1$–$C_6$ alkyl is selected from the group consisting of methyl, ethyl, isopropyl, and butyl.

5. The composition according to claim 1, wherein said ethylenically unsaturated monomer is selected from the group consisting of acrylates, methacrylates, vinyl pyridines, vinyl ethers, acrylamides, methacrylamides, pyrrolidones, and styrenes.

6. The composition according to claim 1, wherein said fragrance comprises a liquid, a solid, a vapor, or a combination of any of the foregoing.

7. The composition according to claim 1, wherein said fragrance comprises a mixture of two or more essential oils.

8. The composition according to claim 7, wherein said essential oils are independently selected from the group consisting of d-limonene, eugenol, orange, lemon, eucalyptol, and clove oil.

9. The composition according to claim 1, comprising a microsphere.

10. The composition according to claim 1, wherein said acrylic acid monomer comprises from about 40 to about 60 percent by weight of said polymer.

11. The composition according to claim 1, wherein said fragrance is adapted to impart an odor or smell to, or to enhance an odor or smell of, a substrate.

12. The composition according to claim 1, wherein said substrate is selected from the group consisting of air fresheners, laundry detergents, fabric softeners, deodorants, and lotions.

13. The composition according to claim 1, wherein said copolymer is pH adapted to release said fragrance at the desired pH.

14. The composition according to claim 13, wherein said copolymer further comprises a pH sensitive group selected from the group consisting of a carboxyl group, an amine group, or a combination thereof.

15. The composition according to claim 1, wherein said composition is adapted to release said fragrance in a timed and sustained manner.

16. A method for preparing a composition, said method comprising
   (a) emulsifying
      (i) an acrylic acid monomer, and
      (ii) at least one ethylenically unsaturated polymerizable monomer to yield unpolymerized globules;
   (b) adding a fragrance to said unpolymerized globules; and
   (c) polymerizing said globules.

17. The method according to claim 16, wherein the polymerization is initiated by free-radical initiator, ultraviolet light, or heat.

* * * * *

UNITED STATES PATENT AND TRADEMARK OFFICE
CERTIFICATE OF CORRECTION

PATENT NO. : 6,375,983 B1
DATED : April 23, 2002
INVENTOR(S) : Martin L. Kantor, Evgueni Barantsevitch and Sam J. Milstein It is certified that error appears in the above-identified patent and that said Letters Patent is hereby corrected as shown below:

<u>Title page,</u>
Item [60], Related U.S. Application Data delete "Provisional application No. 60/019,913, filed on Jun. 19, 1996." and replace with -- Provisional application No. 60/019,913, filed on Jun. 14, 1996. --.

Signed and Sealed this

Twenty-second Day of October, 2002

Attest:

JAMES E. ROGAN
Attesting Officer   Director of the United States Patent and Trademark Office